(12) United States Patent
Mukherjee

(10) Patent No.: US 8,323,181 B2
(45) Date of Patent: Dec. 4, 2012

(54) ENDOSCOPE WITH VARIABLE INCIDENT LIGHT AND LASER SOURCE PLATFORM

(76) Inventor: Apurba Mukherjee, Los Angeles, CA (US)

( * ) Notice: Subject to any disclaimer, the term of this patent is extended or adjusted under 35 U.S.C. 154(b) by 189 days.

(21) Appl. No.: 13/029,464

(22) Filed: Feb. 17, 2011

(65) Prior Publication Data

US 2012/0215065 A1    Aug. 23, 2012

(51) Int. Cl.
*A61B 1/00* (2006.01)
*A61B 1/07* (2006.01)
(52) U.S. Cl. ............... 600/108; 600/130; 600/182
(58) Field of Classification Search .............. 600/108, 600/182, 160, 129, 130, 131, 178
See application file for complete search history.

(56) References Cited

U.S. PATENT DOCUMENTS

| | | | | |
|---|---|---|---|---|
| 4,607,622 A | * | 8/1986 | Fritch et al. ............... | 600/108 |
| 4,928,695 A | * | 5/1990 | Goldman et al. ............ | 600/374 |
| 5,121,740 A | * | 6/1992 | Uram ........................ | 600/108 |
| 5,290,279 A | * | 3/1994 | Bonati et al. .............. | 606/15 |
| 5,419,312 A | * | 5/1995 | Arenberg et al. ........... | 600/108 |
| 5,893,828 A | * | 4/1999 | Uram ........................ | 600/108 |
| 5,919,128 A | * | 7/1999 | Fitch ......................... | 600/166 |
| 6,485,414 B1 | * | 11/2002 | Neuberger ................. | 600/182 |
| 6,936,004 B2 | * | 8/2005 | Utsui ........................ | 600/182 |
| 2003/0045780 A1 | * | 3/2003 | Utsui ........................ | 600/182 |
| 2005/0182294 A1 | * | 8/2005 | Katzman ................... | 600/108 |
| 2005/0203341 A1 | * | 9/2005 | Welker et al. .............. | 600/130 |
| 2006/0106282 A1 | * | 5/2006 | Bala ......................... | 600/108 |
| 2012/0209073 A1 | * | 8/2012 | McWeeney et al. ........ | 600/146 |

* cited by examiner

*Primary Examiner* — John P Leubecker
(74) *Attorney, Agent, or Firm* — Craig A. Simmermon

(57) ABSTRACT

Endoscope and method comprise a micro endoscope with insertion end that is about 1-2 millimeters in outer diameter and includes an optical fiber image bundle, two optical laser fibers, two illumination source optical fiber bundles, along with three focusing lenses for image bundle and laser fibers. Insertion end may be inserted in a female milk duct, other body cavity, or internal organ to inspect for cells and lesions. Visual inspection is aided by the use of special mixtures of light sources to observe the distinction between normal and abnormal cells. If abnormal cells or lesions are detected and the surgeon decides cells or lesions are non-cancerous, the surgeon may then use endoscope to precisely burn, ablate, or otherwise kill abnormal cells at their point of origin on the milk duct, other body cavity, or internal organ. The procedure is minimally invasive and much less costly than many other similarly functioning medical procedures.

6 Claims, 6 Drawing Sheets

ENDOSCOPE WITH VARIABLE INCIDENT LIGHT AND LASER SOURCE PLATFORM

BACKGROUND OF THE INVENTION

1. Field of the Invention

The present invention relates to a micro-endoscope or endoscope apparatus used to visually inspection minute lesions or clusters of cells in a body cavity or interior organ of a human body. Endoscopes are frequently used with laparoscopic surgery where surgery is performed through a small incision or natural opening in the body. A surgeon uses an endoscope to see inside the patient's body.

Endoscope has a distal end that includes an optical fiber bundle with thousands of fibers that is flexible with overall outer diameter of about 1-2 millimeters that is "insertable" into a typical female milk duct, other body cavity, or internal organ.

One application of the present invention relates to the detection of abnormal cells in a human female breast. All breast cancer starts in the lining of the milk ducts. Milk ducts run like tree branches through the breast and culminate in 6-8 openings in the nipple. The widest ducts, near the nipple, are 1.5 mm to 2 mm in diameter. Ducts become microscopic towards the back of the breast near the chest wall. During micro endoscope procedure, the doctor is able to see the lining of the ducts by inserting the flexible fiber optic endoscope into a nipple opening of a milk duct. Endoscope can be used to inspect milk ducts for abnormal cells or lesions. Almost all abnormal conditions of the breast, including breast cancer, originate from the milk duct. If inspection is accomplished early enough in the event of an abnormal condition, the cellular origins of the abnormal conditions may be detected as they occur or at least at a very early stage of the condition, at which point effective measures may be taken to eradicate the condition from the breast at a very early stage, potentially saving the patient's life. This procedure may allow more precise identification of intraductal disease and may result in improved localization of intraductal lesions and may avoid surgery in women with endoscopically normal ducts.

In other applications, endoscope can be used to inspect any part of the body through a small incision, small diameter opening or orifice, or other portal as small as about 1 millimeter in diameter. For example, endoscope may be used to inspect brain tissue, brain ventricles, eye tissue, eye orbital tissue, and other tissue where there is benefit to the use of small incisions on the order of a few millimeters in diameter.

In other applications, endoscope can be used as an endoscopic surgery instrument. The invention includes the capability of targeting certain lesions or cells in the endoscopic viewing area for precise tissue ablation, tissue cutting, tissue resection, or tissue shrinking, without causing damage to surrounding normal cells. The invention allows for delivery of low-energy laser radiation at a specific point or target point within the surgeon's scope of view that may be small enough to focus on a cluster of cells. This is accomplished through the use of a low-energy marking laser along with a low-energy ablation, cutting, resection, or shrinking laser situated within the endoscope apparatus, where the optical fibers for such are included within a 1-2 millimeter outer diameter insertable distal end. If tissue ablation/cutting/resection is accomplished early enough in the event of an abnormal condition, the cellular origins of the abnormal conditions may be eradicated at a very early stage, thereby arresting the abnormal condition before it propagates.

2. Description of Related Art

It has been conventionally known that flexible optical fibers (fiber optics) can be inserted into small narrow body cavities or incisions where the fibers allow the surgeon to effectively see inside the small narrow body cavity or incision with non-invasive or minimally invasive procedural effects on the patient. Prior art endoscopes use various types of optical fibers to project images from inside of the patient's body to the outside where the surgical team may view them and use such views to guide them through the surgical procedure. Flexible optical cables are typically optically connected to cameras that are typically electrically connected by one or more cables to one or more computers that may analyze and present the data in any number of ways to many different devices that prove to aid the surgeon with any number of non-invasive or minimally invasive surgical procedures.

Further it has been conventionally known that flexible optical fibers may be used to transmit laser light from outside of the patient's body to the inside surgical area, where the laser light may be used to help perform the surgical procedure by cutting or ablating tissue, for instance.

This invention provides an endoscope with special illumination capabilities along with special surgical capabilities. This invention is first to provide the capability for a surgeon to visually inspect a milk duct or other body cavity or internal organ with the capability of illuminating a group of target cells in the patient's body with two distinct illumination sources that may be used simultaneously, so that when each illumination source characteristics are used to complement each other, where characteristics include the wavelength, intensity, coherence, phase, and polarization of the light source. The invention causes normal and abnormal cells in the target area to become much more visually distinguishable, where cells look differently than if being viewed by only one or multiple light sources with similar characteristics. When the two light sources have characteristics that complement each other, the change in visual characteristics of the cells renders distinction between normal and abnormal cells in the target area quite apparent.

Moreover, this invention also provides the simultaneous capability of targeting the abnormal cells with two distinct laser sources, along with two special light sources, where the two laser sources can be used to precisely ablate or otherwise burn abnormal cells without damaging surrounding normal cells.

BRIEF SUMMARY OF THE INVENTION

Endoscope comprises an insertion end with a distal tip that is a long thin member about 1-2 millimeters in outside diameter that may be inserted into the patient's body. Insertion end comprises an image-focusing lens optically connected to an image optical fiber bundle, at least two laser focus lenses, each optically connected to one of at least two laser optical fibers, and at least two illumination optical fibers bundles, where the distal ends of said fibers are positioned to shine light onto certain target area and said lenses are trained or positioned to focus on the same said target area. Endoscope further comprises at least two optical illumination ports each optically connected to an illumination source optical fiber bundle. Endoscope further comprises at least two laser ports each optically connected to a laser source optical fiber. Endoscope further comprises a view platform optically connected to the image optical fiber bundle. Endoscope further comprises a surgeon's handle point through which the surgeon may manipulate the insertion end and distal tip within the patient's body.

Endoscope provides the capability to simultaneously shine one or more coherent light sources onto a laparoscopic target area to create more distinguishable viewing characteristics of normal and abnormal cells in the laparoscopic target area.

Endoscope provides the capability to simultaneously shine one or more distinct light sources onto a laparoscopic target area to create more distinguishable viewing characteristics of normal and abnormal cells in the laparoscopic target area.

Endoscope provides the capability to deliver laser energy to ablate, cut, burning, or resect to correct a problem, just after visual inspection of the problem, and during the same medical procedure in order to ablate, cut, burn, resect, or otherwise correct abnormal cells detected.

Endoscope provides the capability to quickly change light sources incident upon the target area, whether coherent or incoherent light sources, to provide an additional method of making more distinguishable by sight normal and abnormal cells in the target area.

DEFINITION LIST

| Term | Definition |
|---|---|
| 1 | Eyepiece |
| 2 | Focus Ring |
| 3 | Body Coupler |
| 4 | Scope Assembly |
| 5 | Fiber Optic Post I (Light Port I) |
| 5A | Fiber Optic Post II (Light Port II) |
| 6 | Image Bundle, Illumination Bundle I, and Illumination Bundle II |
| 6A | Image Bundle, Illumination Bundle I, Illumination Bundle II, Laser Fiber I, and Laser Fiber II |
| 7 | Laser Fiber I Extended Lead |
| 8 | Surgeon's Handle Point |
| 9 | Luer Lock Connector |
| 10 | Laser Fiber Connector I (Laser Port I) |
| 11 | Laser Fiber II Extended Lead |
| 12 | Laser Fiber Connector II (Laser Port II) |
| 13 | Insertion Fiber Bundle containing Image Fiber Bundle, Illumination Bundle I, Illumination Bundle II, Laser Fiber I, and Laser Fiber II |
| 13A | Distal End or Tip of Insertion Fiber Bundle |
| 14 | Milk Ducts of Human Breast |
| 15 | Data Cable connecting Camera to Computer |
| 16 | Camera |
| 17 | Camera Lens |
| 18 | Camera Coupler |
| 19 | Computer or Monitor |
| 20 | Normal Cells |
| 21 | Abnormal Cells |
| 23 | Introducer Assembly |
| 24 | Introducer Fluid Channel |
| 25 | Introducer Fluid Connector |
| 26 | Introducer Catheter |
| 32 | Outer sheath of Insertion Fiber Bundle |
| 33 | Illumination Optical Fiber Bundle I |
| 34 | Illumination Optical Fiber Bundle II |
| 35 | Image Optical Fiber Bundle |
| 36 | Laser Fiber I |
| 36A | Laser Fiber II |
| 43 | Laser I Focus Lens |
| 45 | Image Bundle Focus Lens |
| 46 | Laser II Focus Lens |

DETAILED DESCRIPTION OF THE INVENTION

Figure 1:
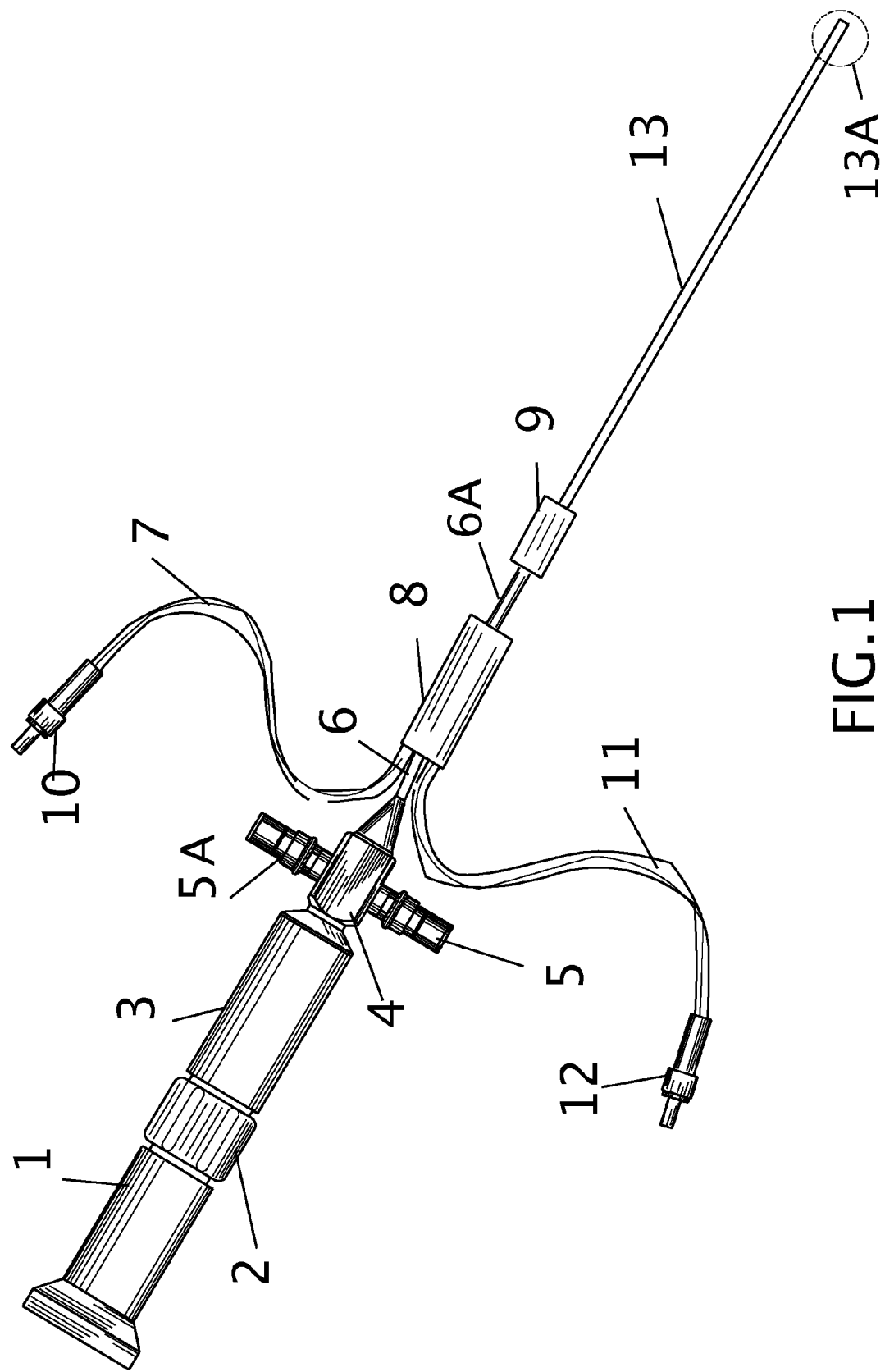
FIG. 1 is a top plan view of endoscope.

Referencing FIG. 1, endoscope has a proximal end (upper left corner of figure) and a distal end (lower right corner of figure). Proximal end includes a subassembly comprising items 1, 2, and 3 that is essentially a long hollow cylindrical body with optical lenses inside. The surgeon looks into item 1 (eyepiece) or a camera may connect with it to view cells in the target area. The distal end, items 13 and 13A, may be inserted into the patient's body. Distal end is a low-friction flexible member that includes fiber optics that function to bring light to and from the patient's body cavity or internal organ.

Endoscope comprises an eyepiece 1, body coupler 3, and scope assembly 4. Scope assembly 4 comprises a bundle of optical fibers called an image bundle 35 that essentially runs the full length of flexible cables 6, 6A, and 13, extending to the distal end of endoscope 13A. Image bundle 35 is a bundle of about 6,000-30,000 optical fibers that are each about 0.5-1.0 millimeters in outer diameter and about 0.5-2 meters long. Each optical fiber is one flexible continuous piece. Optical fibers are typically made of quartz or glass silica but could be made of any material that function as follows. An optical fiber passes light down the center of the fiber, where passing light is basically continuously reflected off of the outer surfaces of the fiber, thereby forcing the light to travel the full length of the fiber to pass out of the other end of the optical fiber. Light is kept in the core of the fiber as a result of total internal reflection.

Eyepiece 1 may be replaced with camera coupler 18 and camera 16. Camera 16 includes camera lens 17. When operating in this mode, camera 16 produces and processes images from the target area of the patient. These images can then be sent to a computer or viewer 19 through data cable 15. Images may be recorded on computer or viewer 19.

Scope assembly 4 further comprises an image bundle focus lens 45, located at the distal end of the image bundle 35. Every fiber of image bundle is optically connected to image bundle focus lens 45 so that light waves may pass from the interior of the patient's body through image bundle focus lens 45 and into all fibers of image bundle 35 without significant reflection or refraction loss. Thus, optical connections function to perform such connections with minimal reflection or refraction loss. Typically, optical connections are accomplished by pressing, terminating, or attaching polished optical fiber end(s) to the fiber, fibers, lens, or transition glass of the other optical device, where such is done by connector means, where standardized connectors, typically male and female, may be reversibly optically connected to press and hold these optics together. In this case, fiber ends are polished and precisely glued in place next to lens 45 with a special optical epoxy (not shown). Image bundle focus lens 45 is located at the center of the cross-section of the insertion end 13A. Image bundle focus lens 45 is a lens with outside diameter of about 500 microns (μm). Image bundle focus lens 45 functions to focus the scattered light reflecting off of the target area and into image bundle 35. Image bundle focus lens 45 focuses scattered light into parallel light that may more easily travel into, through, and out of image bundle 35 and on to the surgeon's view.

Scope assembly 4 includes all fiber bundles, which are optically connected components in insertion end 13A and all ports 5, 5A, 10, and 12. Scope assembly 4 cannot be disassembled without disrupting the optical connections therein. Thus, insertion portions 13 and 13A are permanently connected to scope assembly 4.

From scope assembly 4, light waves originating from the interior of the patient's body then enter body coupler 3, which comprises at least two lenses (not shown), one lens at each end of body coupler 3. Body coupler distal lens functions to focus the generally "scattered" light from the interior of the patient's body emanating from scope assembly 4 into "parallel" light where light waves emanating from the other side of this lens are traveling generally in one direction parallel to the longitudinal axis of body coupler 3. Eyepiece 1 comprises at least one lens (not shown). Body coupler proximal lens along with eyepiece lens are then used in tandem to focus the parallel light onto the surgeon's eye or camera array connected to a monitor, computer, or similar electronic device capable of receiving and displaying imaging signals from a camera array.

In order to accomplish this focusing, body coupler 3 further comprises a focus ring 2. Focus ring 2 functions to mechanically move by threaded means body coupler 3 longitudinally in relation to the body coupler proximal lens. By changing the distance between eyepiece lens and body coupler proximal lens, the plane of focus inside the patient's body may be adjusted, thereby allowing the surgeon to change his plane of focus inside the patient's body. The length of focus of the endoscope in the target area in best mode is about 3 millimeters, extending distally outward from the distal tip of insertion bundle 13A. The technology of eyepiece 1, focus ring 2, and body coupler 3 and their interaction with scope assembly 4 are well known in the art of endoscopes.

Scope assembly 4 further comprises two fiber optic posts or light ports 5 and 5A and two laser fiber connectors or laser ports 10 and 12. These ports are used to connect to external illumination sources and/or external laser sources where these light sources may be used as "incident light" to shine onto the target area inside the patient's body. Light ports 5 and 5A provide the ability to optically connect to typical light sources such as: incandescent; light-emitting diode; gas discharge, including xenon, halogen, metal halide; or other light source. Such light sources are typically incoherent in that their wave fronts are generally spherical and travelling in diverging directions or are otherwise without constant relative phase.

Laser ports 10 and 12 provide the capability to optically connect to typical laser sources like: Diode Pumped Solid-State Lasers, Fiber Lasers, Green Lasers, Diode Lasers, $CO_2$ Lasers, YAG Lasers, HeNe, Argon-ion, HeAg, NeCu, KTP/ Nd:YAG, Nd:YVO4, Nd:YVO4, Nd:YLF, Nd:YAG, Yb:YAG, Yb:KGW, Yb:KYW, Yb:SYS, Yb:BOYS, Yb:CaF2, Ti:Sapphire, or other lasers. Laser ports 10 and 12 have extended leads 7 and 11 respectively to allow for easier laser connection and to allow placement of heavier laser equipment away from patient working area for the surgeon. Laser light sources are typically coherent in that their wave fronts are travelling in synchronized fashion, in phase, and propagating in parallel, in the longitudinal direction of the endoscope or fiber. Thus, endoscope provides the capability to shine as incident light into a milk duct, other body cavity, or incision, two separate incoherent light sources, as well as two separate coherent light sources. Also, endoscope provides the ability to vary phase, intensity, wavelength, polarization, and other characteristics of the light sources on an individual basis.

Light ports 5 and 5A are essentially hollow cylindrical members, with optical glasses inside, used as connectors to reversibly optically connect with other connectors of light sources. Light ports 5 and 5A each comprise a threaded post that may be reversibly attached by threaded means to a female connector of an external light source (not depicted). Light ports 5 and 5A each further comprise an optical glass that mates with another optical glass in the female optical connector of the light source.

Figure 4:
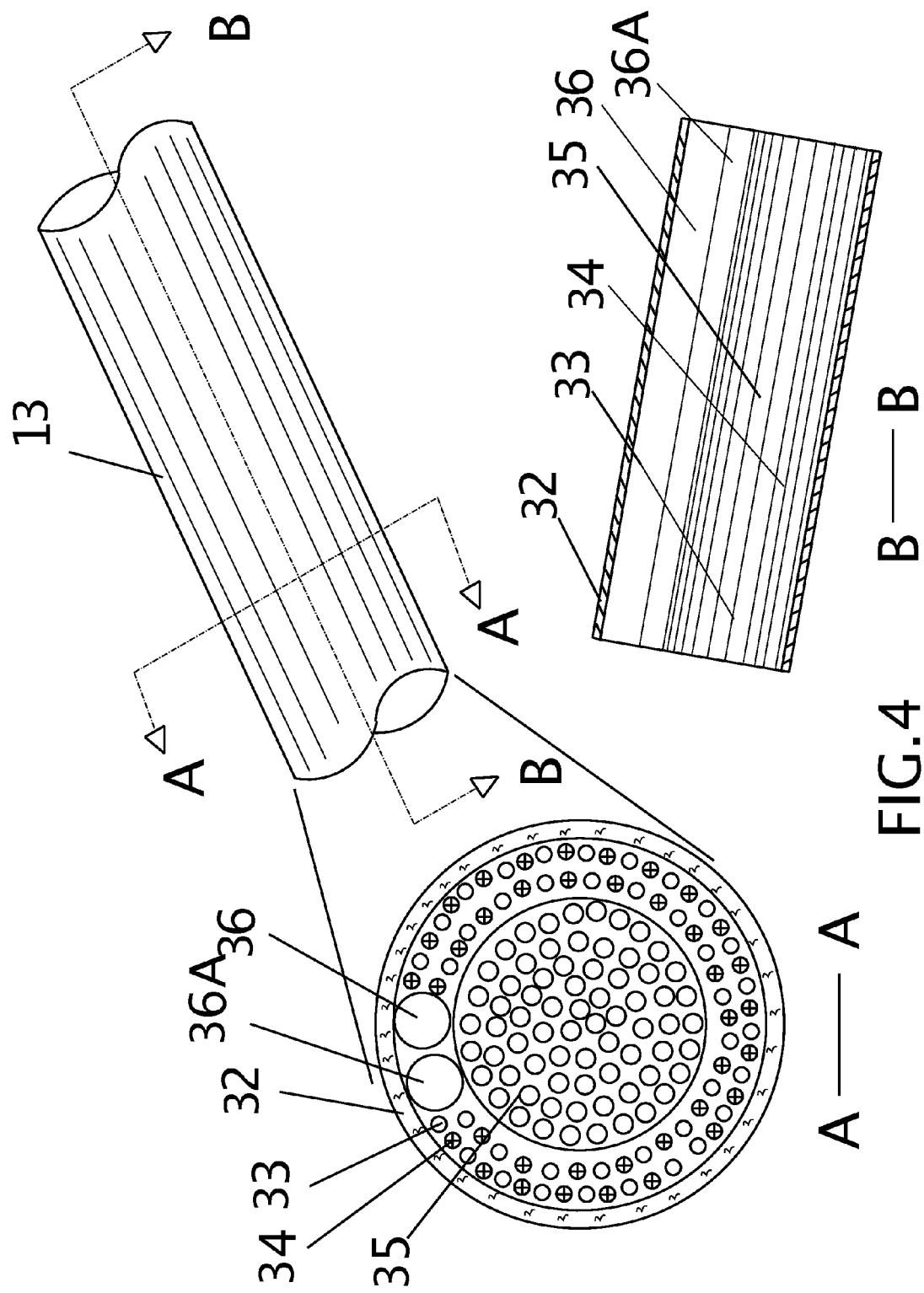
FIG. 4 is a blow-up view of insertion fiber bundle or the insertion end of endoscope, along with two corresponding cross sectional views thereof.
Figure 5:
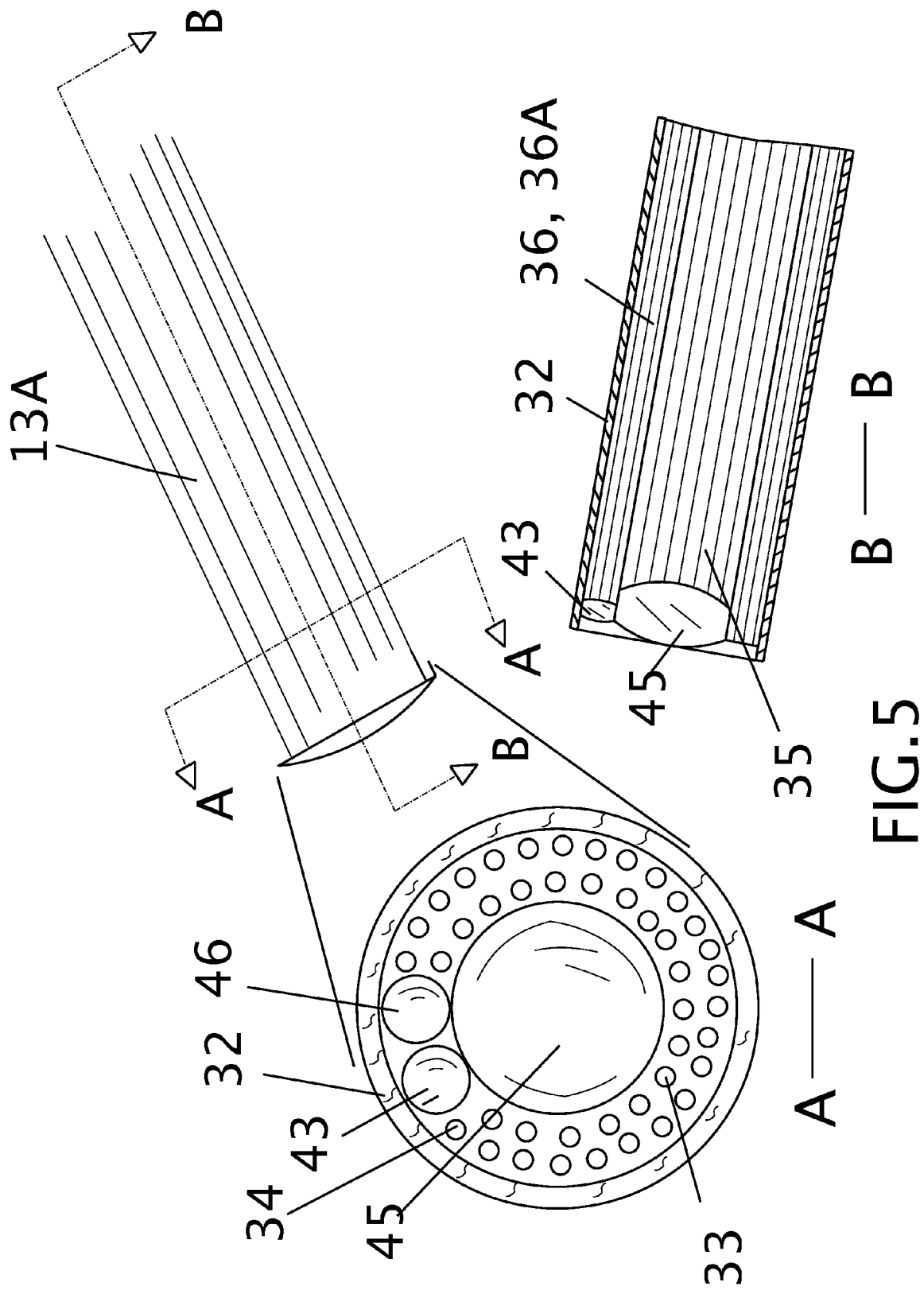
FIG. 5 is a blow-up view of the distal end of insertion fiber bundle or the tip of insertion end of endoscope, along with two corresponding cross sectional views thereof.
Figure 6:
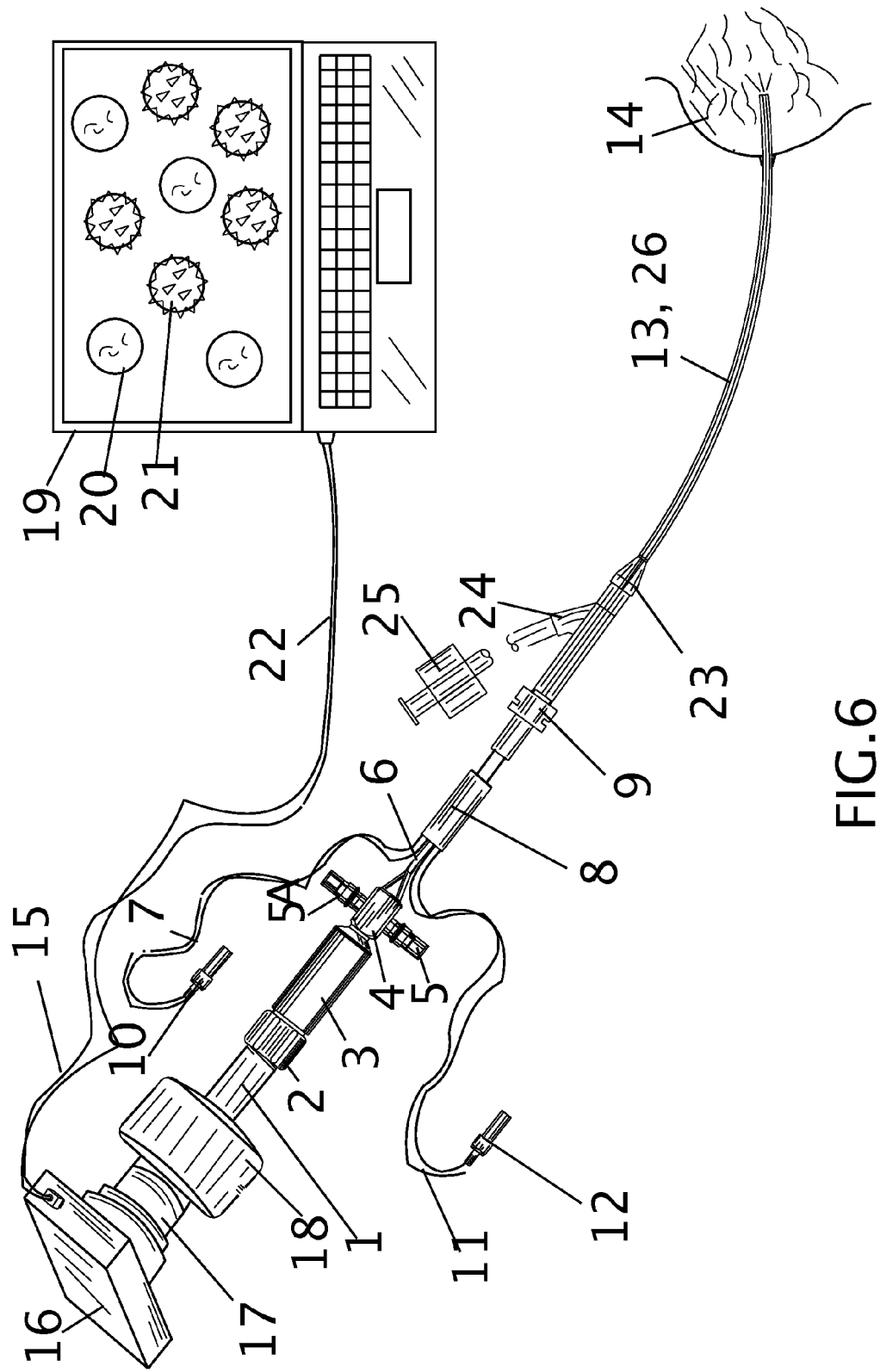
FIG. 6 is side perspective view of endoscope with introducer, camera, and monitor attached, depicted while inserted into a patient's body, where the monitor depicts the high degree of differentiation between normal and abnormal cells that is provided by endoscope with this arrangement.

Scope assembly 4 further comprises illumination bundles I and II, which are items 33 and 34 respectively. Each illumination bundle 33, 34 is a bundle of about 6,000-30,000 optical fibers that are each about 0.5-1.0 millimeters in outer diameter and about 0.5-2 meters long. The proximal ends of each fiber are optically connected to optical glass of light ports 5 or 5A. The proximal ends of each fiber are substantially perpendicular to longitudinal axis of the fiber and are polished to allow for minimal reflection or refraction as light passes from the illumination source optical connector to the optical glass of light port and into individual fibers of illumination bundles 33 and 34. All fibers in illumination bundles 33 and 34 are packed around image bundle 35 along the full lengths of 6, 6A, 13, and 13A. See cross sectional views on FIGS. 4 and 5 for depictions of this arrangement. Distal ends of image bundle 33 and 34 are alternated around image bundle focus lens 45, as shown in the cross section, so that the different incident lights of 33 and 34 will be evenly distributed over the whole target viewing area. The distal ends of each fiber, at 13A, are substantially perpendicular to longitudinal axis of the fiber and are polished to allow for minimal reflection or refraction as light passes from the fibers and into the patient's body cavity. Thus, with bundles 33 and 34, light passes from an external light source connector, into 5 or 5A, then into individual fibers of bundles 33 or 34, to exit there from, in a circular pattern of fibers surrounding the image bundle focus lens 45. See FIGS. 4 and 5.

Scope assembly 4 further comprises laser fibers I and II, which are items 36 and 36A respectively. Each laser fiber 36, 36A is a one-piece optical fiber about 100-250 microns (μm) in outer diameter and about 0.5-2 meters long. The proximal ends of each fiber are substantially perpendicular to longitudinal axis of the fiber and are polished to allow for minimal reflection or refraction as light passes from the laser source optical connector (not depicted) and into laser fiber 7 or 11. Laser ports 10 and 12 are each industry standard laser source fiber optic adapters, used as connectors to reversibly optically connect to other optical connectors of lasers. Laser ports 10 and 12 comprise a threaded post that may be reversibly attached by threaded means to the female optical connector of an external laser source. Proximal ends of each fiber 36 and 36A are pressed against optical glass or optical fiber in the female optical connector of the laser source. The distal ends of each fiber, at 13A, are substantially perpendicular to longitudinal axis of the fiber and are polished to allow for minimal reflection or refraction as light passes from the fibers and into laser focus lens 43 or 46. Thus, light passes from an external laser source connector, into 10 or 12, into fiber 36 or 36A, to run the full length of 7 or 11 and 6, 6A, 13, and 13A, to exit there from into laser focus lens 43 or 46, respectively.

Scope assembly 4 further comprises laser focus lenses 43 and 46, which are located at the distal end of endoscope at 13A. See FIG. 5. Laser focus lenses 43 and 46 are located offset to the center of the cross-section of the insertion end 13A. Laser focus lenses 43 and 46 each have outside diameters of about 100-250 microns (μm). Laser focus lenses 43 and 46 function to focus the parallel laser light travelling down fibers 36 or 36A down onto a specific point or focal point in the target area. Ideally, the focal points of both 43 and 46 will be identical, so that both lenses focus their laser light onto the same point. This way, one laser source may act as a marking or targeting laser while another laser source may act as the actual burning or ablating laser. A targeting laser is required to accomplish the precise cell ablation or resection without damage to surrounding normal cells. Alternately, focal points may be located slightly adjacent to each other in the target area for lenses 43 and 46 respectively. Scope assembly 4 is assembled so that lenses 43 and 46 are optically connected to fibers 36 and 36A respectively, so that fibers 36 and 36A are connected to lenses 43 and 46, respectively, to minimize reflection and refraction caused by the transition, in permanent fashion, to withstand flexing as 13 and 13A are inserted into the patient's body.

There are certain "recipes" of incident light, so to speak, where wave-interference between the different light sources causes normal cells 20 and abnormal cells 21 in the target area to become much more visually distinguishable. In other words, due to the wave nature of light, the use of two or more coherent light sources from different incident angles upon cells in the target area can sometimes cause different types of cells in the target area to become much more visually distinguishable. For instance, one visible light laser may be used as two incident coherent light sources by splitting the laser and feeding 50% through laser port 10 and 50% through laser port 12 thereby shining the target area with two exactly coherent light sources, shining at different angles upon the target area. When this occurs, the more apparent visual distinguishability effect has been seen to occur. Likewise, two separate visible lasers of the same type may be used, where one is connected to port 10 and the other to port 12 thereby shining the target area with identical light waves with constant relative phase from two separate light sources shining at different angles upon the target area. Likewise, when this occurs, the more apparent visual distinguishability effect has been seen to occur.

It is believed that at least two coherent light sources shining from different incident angles is required for the aforementioned more apparent visual distinguishability effect to occur. This is due to the wave nature of light, where coherent light waves interfere constructively with each other, to yield different characteristics of light reflected from the target area than would be otherwise if incoherent incident sources were used. This property of light was initially investigated and used to create the first holographic or three-dimensional images. This type of light sources was required to make the holograms. To maximize the difference in incident angles between these light sources, lenses 43 and 46 would be placed at opposite ends of distal end of insertion fiber bundle 13A, which arrangement is not depicted in FIG. 5.

On the other hand, the surgeon may choose to simply change light sources by connecting different non-coherent light sources available in the operating room in various combinations in order to view cells in the target area for differences resulting from the variation in lighting of the target area. A benefit of the design is that it allows faster variation or changing of different light sources. Also, the surgeon's team may work ahead by completing any connections and disconnections of light sources before the surgeon actual calls for an incident light change. The endoscope provides the capability to use four distinct incident light sources on the target area thereby dramatically increasing the likelihood of attaining the more distinguishable normal 20 and abnormal 21 cell characteristics.

Of course, the surgeon may choose to use both laser incident light and incoherent incident light. For instance, the use of one or more LED light sources in combination with one or more visible light laser incident light sources sometimes causes different types of cells in the target area to become more distinguishable.

Insertion portions of endoscope 13 and 13A further comprise a sheath or coating 32 on its outer surface, made of low-friction flexible material that is FDA-approved for internal body contact. In best mode sheath 32 is made of polyamide, but may be other material that is functionally equivalent. Coating 32 functions to protect optical fibers, keep optical connections together, and to allow the endoscope to easily slide in and out of a the milk duct, other body cavity, incision, or introducer 23. Insertion portions 13 and 13A represent advanced technological achievement given that all optical fibers and lenses mentioned above are assembled inside the 1-2 millimeter outside diameter insertion fiber bundle 13 and insertion end 13A. Insertion portion 13 is also flexible so that it may be formed into an arc with 35-millimeter radius without breaking any optical fibers enclosed therein. 13 and 13A can be about 6-30 cm long.

Figure 2:
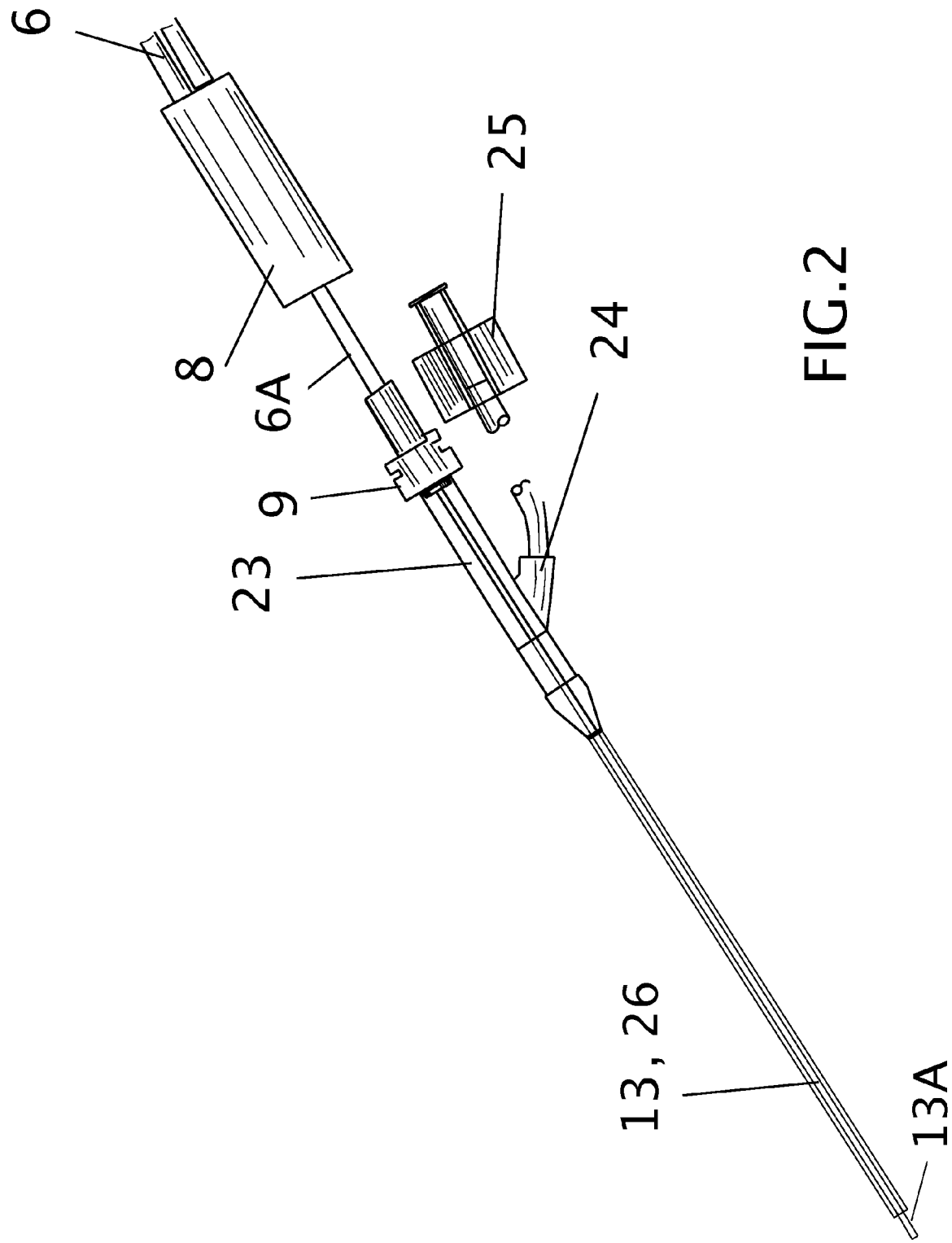
FIG. 2 is a blow-up view of the distal end of endoscope where the distal end has been pre-inserted into an introducer, where the use of an introducer is typically used to help insert the distal end into the patient's body, and provide sterile water flow in front of the distal end of endoscope.
Figure 3:
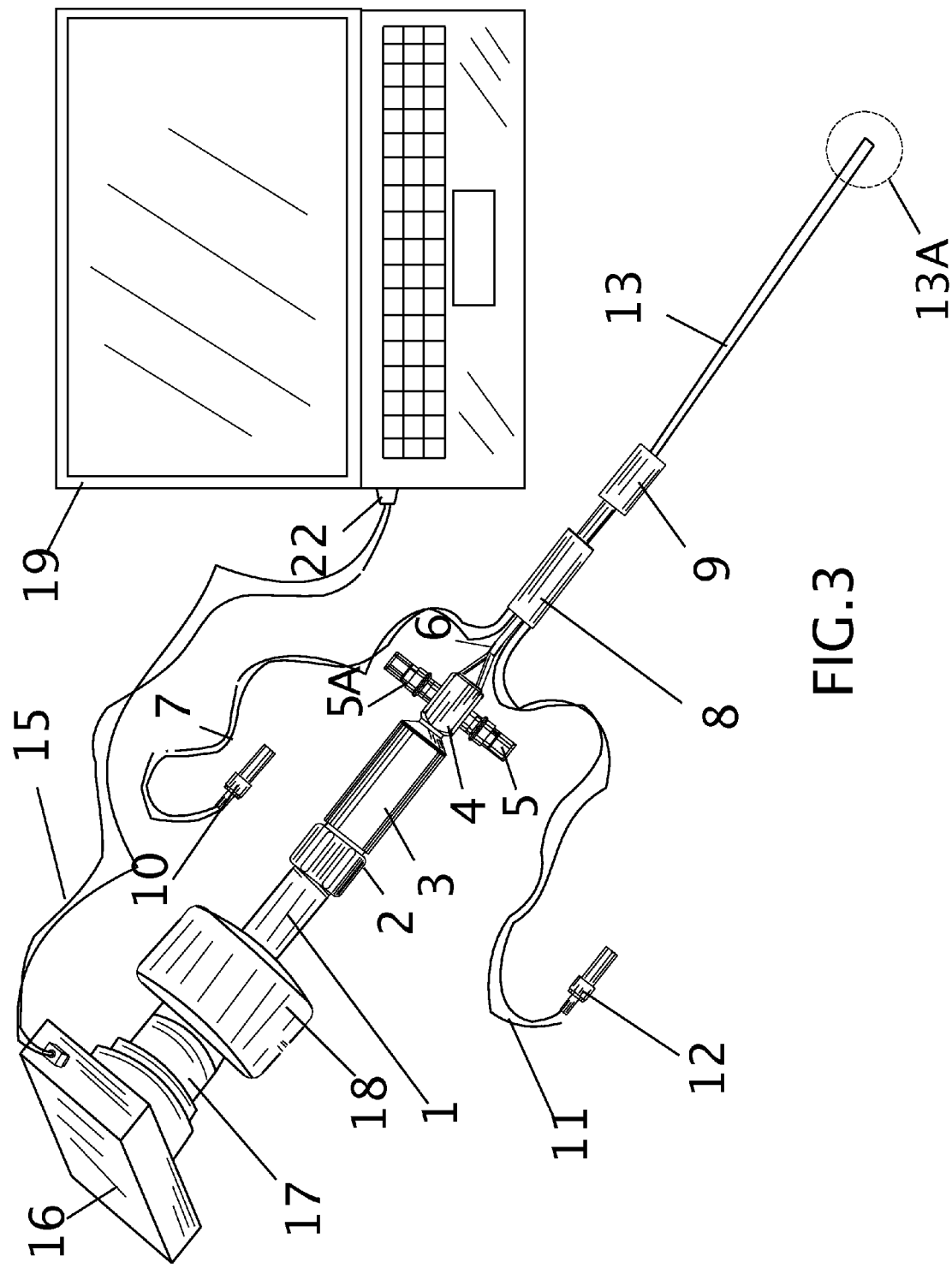
FIG. 3 is a side perspective view of endoscope with camera and monitor attached, as is also typical for endoscopic viewing of a patient's body.

The endoscope must be pre-inserted into an introducer 23 before insertion into a nipple/milk duct. An introducer 23 allows for the use of a lubrication fluid to help glide the distal end of the introducer or catheter 26 (with 13 and 13A inside of it) into the nipple/milk duct. In most case saline solution is used for lubrication fluid. The saline solution flow enlarges the milk duct and allows the endoscope move inside the duct without damaging the duct linings by the tip of the endoscope. First elements 13 and 13A of endoscope are inserted into the catheter 26 of introducer 23 as shown in FIG. 2. The inside diameter of 26 is slightly larger than the 1-2 millimeter outside diameter of 13 and 13A. This allows saline solution to travel between these diameters so to speak. Then, luer lock connector 9 on endoscope is connected to another luer lock connector on introducer 23. Next, connector 25 on introducer 23 is connected to another connector attached to the sources of saline solution (not shown) to form a fluid tight connection. In this way saline solution flows by gravity into connector 25, to fill catheter 26 with saline solution. Saline solution then flows distally down 26, flowing around 13, to exit from the distal end of 26. After 13A is inserted into the nipple/milk duct, saline solution flow may be turned on to allow saline solution into the milk duct, which expands the milk duct. In this way, milk duct is expanded to allow for easier insertion of 13A. As 13A is inserted more, it opens more of the milk duct, thereby allowing further insertion, and so on until endoscope is inserted to location that the surgeons desires. Saline solution also spreads out the mild duct lining which helps the surgeon see clusters of cells lesions. After filling the milk duct, saline solution is absorbed into the patient's system. Saline solution flows by gravity or is pumped at a very at low pressure and low flow rate to achieve the characteristic described above.

Catheter portion 26 of introducer 23 is typically made of stainless steel or other material approved for insertion into the body. Catheter portion 26 of introducer 23 may require special design and construction to mate with and perform properly with endoscope. Likewise, special design and construction of 26 may be required for specific body cavities or specific internal organ inspection. Thus, different procedures may require different introducers.

The method of using endoscope includes first obtaining an endoscope as described above.

Next, the surgeon must consider what incident light sources will be required in the procedure. All such incident light sources should be assembled. The first two such incident light sources should be connected by the appropriate fiber optic cables to fiber optic posts I and II, 5 and 5A.

Next, the surgeon may consider if any laser sources will be required in the procedure, noting that laser sources may be used for incident light sources or for common laser purposes such as tissue ablation, tissue cutting, tissue resection, or tissue shrinking. All such laser sources should be assembled. The first two such laser sources should be connected to laser fiber connectors I and II, 10 and 12.

The method of use of endoscope may include preparation of the duct, orifice, natural opening, or incision to numb the area and to dilate the duct, orifice, natural opening, or incision. Such preparation may include administration of topical lidocaine, injected lidocaine, or similar about 30 minutes prior to insertion of the endoscope into the duct, orifice, natural opening, or incision. Alternatively, local or general anesthetic may be used to render insertion of the endoscope more comfortable for the patient. Additionally, in the case of milk duct insertion into a breast, the breast may be massaged to promote nipple-aspirate fluid, a maneuver that helps to visually identity a ductal opening.

The duct, orifice, natural opening, or incision may be further expanded using insufflator, a dilator, or introducer or combination thereof. With insufflation, a gas is injected or pumped in the duct, orifice, natural opening, or incision thereby enlarging the duct, orifice, natural opening, or incision to more easily allow insertion and desired movement of the endoscope within the duct, orifice, natural opening, or incision. An introducer works the same way however a liquid and not a gas is injected or pumped in the duct, orifice, natural opening, or incision to enlarge. A dilator uses a mechanical means to enlarging the duct, orifice, natural opening, or incision.

Best mode procedure is as follows. Injection of approximately 1 cc of subcutaneous lidocaine without epinephrine into the nipple until it is fully distended. This will not only achieve adequate anesthesia but also highlight the duct openings as dimples on the nipple surface and relax the lactiferous sinus sphincter. An aspirator can be used to try to elicit nipple aspirate fluid from one or more ducts to aid in ductal opening identification, however, ducts without obvious fluid can also be cannulated with the distal end of endoscope. Once a possible location of a duct is identified, the ductal opening is gently probed with a dilator to confirm that it is indeed a duct. Additional larger dilators can be used to enlarge the duct. The largest should be left in the duct opening while the endoscope is prepared. Next, the introducer is prepared with a 10 cc of saline for insufflation. The dilator is removed from the duct to be studied and the introducer with its cannula and saline insufflation is inserted into the duct. The cannula is removed, insufflation is conducted as described above, and the distal end of endscope is passed through the introducer.

After the duct, orifice, natural opening, or incision is expanded (if required), incident light sources are turned on and the endoscope is inserted and advanced into the duct, orifice, natural opening, or incision. The surgeon then manipulates the insertion end 13 of endoscope within the duct, orifice, natural opening, or incision in order to position distal tip 13A as desired. The surgeon manipulates the endoscope by holding onto surgeon's handle point 8 and manipulating it accordingly.

While inserting and manipulating endoscope, the surgeon has direct vision and examination of all tiers or branches of the duct, orifice, natural opening, or incision through eyepiece 1, camera 16, or computer or monitor 19. Endoscope may be inserted into the duct, orifice, natural opening, or incision up to a blockage point caused by natural narrowing, one or more lesions, or other obstruction.

The surgeon may try all available combinations of incident light sources using all four ports 5, 5A, 10, and 12. For instance, if two different laser sources and two different illumination light sources are available to the surgeon, a total of 16 different lighting options may be surveyed to see which combination that provides illumination that yields the largest amount of visual distinguishability between normal and abnormal cells.

If an abnormal lesion is found, the extent of the disease is marked out on the skin at the most proximal and most distal lesions, and axial extent is marked when disease is present in multiple peripheral branches of the same ductal tree, duct, orifice, natural opening, or incision.

If any intraluminal pathology (abnormal cells or tissues) is identified, the surgeon may mark it for biopsy, or may use the laser capability of the endoscope system to burn, ablate, cut, shrink, or resection the abnormal cells or tissues.

If tissue ablation, cutting, resection, or shrinking is required, the following procedure should be followed. A marking laser is connected to connector 10 or 11. A marking laser is a cold laser that produces a visually apparent focal point where such focal point does not heat patient tissue. Next, a second laser is connected to connector 10 or 11. The second laser produces enough energy to affect target cells when shined onto the target cells. The surgeon then turns on the marking laser and manipulates the insertion end of endoscope so that the marking laser is shining on one or more target abnormal cells. The surgeon then turns on the second laser to burn, ablate, cut, shrink, or resect the abnormal cells or tissues. The surgeon repeats these steps as necessary to burn, ablate, cut, shrink, or resection all abnormal cells or tissues as required.

The findings of the endoscope can be recorded in a computer hard drive or monitor 19 through cable 15. Both still images and video clips can be recorded as desired by the surgeon. The surgeon may record the procedure before, during and after the endoscope procedure.

The above steps of endoscope procedure may be performed as an outpatient office procedure in a doctor's office under local sedation or in an operating room environment where the patient in under general anesthesia.

What is claimed is:

1. An endoscope comprising:
    a flexible insertion end that is 0.5-2.0 millimeters in outside diameter and 6-30 centimeters in length, said flexible insertion end comprising: a distal tip, an image optical fiber bundle, at least two laser optical fibers, at least two illumination optical fiber bundles, and a low-friction flexible outer sheath, wherein,
        said distal tip comprises: an image bundle focusing lens, at least two laser focusing lenses, and the optical fiber distal ends of said at least two illumination optical fiber bundles, said image optical fiber bundle comprises 6,000-30,000 optical fibers that are each 30-40 microns in outer diameter and 0.5-2.0 meters long, where their distal ends are mounted essentially flush with the distal end of said flexible insertion end with excess length of said 0.5-2.0 meters extending proximally toward the surgeon, each of said at least two laser optical fibers comprises a one-piece optical fiber that is 100-250 microns in outer diameter and 0.5-2.0 meters long, where each distal end of said at least two laser optical fibers is mounted to the proximal end of one of said at least two laser focusing lenses, where the distal ends of said at least two laser focusing lenses are each mounted essentially flush with the distal end of said flexible insertion end with excess length of said 0.5-2.0 meters extending proximally toward the surgeon, each of said at least two illumination optical fiber bundles comprises a bundle of 50-200 optical fibers that are each 40-50 microns in outer diameter and 0.5-2.0 meters long, where their distal ends are mounted essentially flush with the distal end of said flexible insertion end with excess length of said 0.5-2.0 meters extending proximally toward the surgeon, and said low-friction flexible outer sheath encapsulates said flexible insertion end and said distal tip to form an air and liquid tight seal around said image optical fiber bundle, said at least two laser optical fibers, said at least two illumination optical fiber bundles, and said image bundle focusing lens, and said at least two laser focusing lenses, a surgeon's handle point;
at least two light source optical connector ports;
at least two laser source optical connector ports; and
a surgeon's view platform, wherein, said image bundle focusing lens is optically connected to the distal end of said image optical fiber bundle and the proximal end of said image optical fiber bundle is optically connected to said surgeon's view platform, said at least two laser focusing lenses are each optically connected to the distal end of one of said at least two laser optical fibers and the proximal ends of said at least two laser optical fibers are each optically connected to one of said at least two laser source optical connector ports, where the number of laser focusing lenses, laser optical fibers, and laser source optical connector ports must match, said at least two light source optical connector ports are each optically connected to one of the proximal ends of said at least two illumination optical fiber bundles, where the number of illumination optical fiber bundles and light source optical connector ports must match, said surgeons handle point comprises a rigid oblong shaped member with a void running longitudinally through the middle of the oblong shape through which said image optical fiber bundle, said at least two laser optical fibers, and said at least two illumination optical fiber bundles pass, wherein said rigid oblong shape provides a handle point from which to hold optical fibers running there through such that movement of the oblong shape projects movement of said flexible insertion end while it is positioned inside the patient's body.

2. An endoscope as recited in claim 1, wherein each said at least two light source optical connector ports is capable of optically connecting with a connector from: a light-emitting diode, gas discharge, xenon, halogen, or metal halide light source, where the surgeon may switch light sources one at time or may superimpose both light sources to illuminate the target area.

3. An endoscope as recited in claim 1, wherein each of said at least two laser source optical connector ports is capable of optically connecting with a connector from: Diode Pumped Solid-State Lasers, Fiber Lasers, Green Lasers, Diode Lasers, $CO_2$ Lasers, YAG Lasers, HeNe, Argon-ion, HeAg, NeCu, KTP/Nd:YAG, Nd:YVO4, Nd:YVO4, Nd:YLF, Nd:YAG, Yb:YAG, Yb:KGW, Yb:KYW, Yb:SYS, Yb:BOYS, Yb:CaF2, or Ti:Sapphire Laser, where the surgeon may shine onto the target area: one laser for illumination purposes, multiple lasers concurrently for illumination purposes, one laser for illumination along with one laser for marking or targeting certain tissue in the target area, or one laser for marking or targeting certain tissue along with one laser for delivering laser energy to certain target tissue in order to burn or ablate certain tissue.

4. An endoscope as recited in claim 1, wherein said at least two laser focusing lenses are positioned adjacent to each other in said distal tip or apart from each other in said distal tip.

5. A method of using an endoscope comprising:
   a) obtaining an endoscope according to any one of claims 1-4;
   b) connecting one or more incident light sources to said endoscope, wherein, said one or more incident light sources is a: light-emitting diode, gas discharge, xenon, halogen, metal halide, or laser light source;
   d) inserting said endoscope into a patient through an duct, orifice, natural opening, or incision;
   e) viewing the interior of said duct, orifice, natural opening, or incision; and
   g) removing said endoscope from said patient's duct, orifice, natural opening, or incision.

6. A method of using said endoscope as recited in claim 5, further comprising the steps of:
   c) connecting one or more laser sources to said endoscope; and
   f) projecting the energy produced from said one or more laser sources onto tissue in said patient's duct, orifice, natural opening, or incision.

* * * * *